(12) United States Patent
Carnevale et al.

(10) Patent No.: US 7,512,333 B2
(45) Date of Patent: Mar. 31, 2009

(54) METHOD AND APPARATUS FOR POWERING A STROBE FOR RETINAL IMAGING

(76) Inventors: Matthew Carnevale, 26 Foss St., Medford, MA (US) 02155; Denis Miles, 229 Ashland St., Holliston, MA (US) 01746

( * ) Notice: Subject to any disclaimer, the term of this patent is extended or adjusted under 35 U.S.C. 154(b) by 530 days.

(21) Appl. No.: 11/239,938

(22) Filed: Sep. 30, 2005

(65) Prior Publication Data
US 2007/0077054 A1 Apr. 5, 2007

(51) Int. Cl.
*G03B 7/26* (2006.01)
(52) U.S. Cl. .................. 396/205; 396/301; 315/241 S; 315/240
(58) Field of Classification Search .............. 396/205, 396/301; 315/224–225, 230, 237, 240, 241 R, 315/241 S, 287, 308, 86
See application file for complete search history.

(56) References Cited

U.S. PATENT DOCUMENTS 4,005,337 A * 1/1977 Rabe ....................... 315/241 S
4,422,016 A * 12/1983 Kurple .................... 315/241 S
4,613,797 A * 9/1986 Eggers et al. ........... 315/241 R
4,954,753 A * 9/1990 Sikora ......................... 315/219

FOREIGN PATENT DOCUMENTS

GB 2007047 * 5/1979
GB 2137828 * 10/1984

* cited by examiner

*Primary Examiner*—Jay M Patidar
(74) *Attorney, Agent, or Firm*—Robert K. Tendler

(57) ABSTRACT

A lightweight, small, high-voltage power supply for a xenon flash lamp or strobe permits rapid and reliable strobing for retinal imaging. In one embodiment the power supply can develop 500 volts at 720 watt seconds to permit firing the xenon strobe at full power one pulse per second. The power supply, rather than using heavy, bulky transformers, uses a hybrid high-voltage multiplier that involves an AC coupling circuit and a half-wave rectifier, the outputs of which are coupled in series to a capacitor bank to achieve a 500-volt charging source for the capacitor bank. This permits the capacitor bank to be charged with a continuous high voltage so that it can deliver a controlled, reliable high voltage to the xenon strobe.

18 Claims, 6 Drawing Sheets

120 VRMS
170 volts peak

METHOD AND APPARATUS FOR POWERING A STROBE FOR RETINAL IMAGING

FIELD OF THE INVENTION

This invention relates to a power supply for flash lamps used in retinal imaging and more particularly to a transformerless power supply operating off line voltage and voltage tripling to achieve a continuous high-voltage source for charging strobe capacitors.

BACKGROUND OF THE INVENTION

In terms of retinal imaging, in the past it has been the practice to utilize a strobe as a light source for a retinal camera, with the strobe being pulsed as quickly as one and a half times per second to permit the formation of a so-called angiogram for the detection of retinal damage, primarily due to blood leakage. In order to determine the locus of the leak, a patient is injected with dye that goes through the bloodstream in about 30 seconds, at which point it arrives at the back of the eye. At the time that the dye arrives at the back of the eye, a retinal camera is started to capture sequential photographs at roughly one and a half pictures per second so that one can obtain images of the progression of the dye as it passes through the blood vessels in the retina.

The purpose of providing sequential photographs is to be able to ascertain where a leak occurs in the eye, which to view the progression of the dye. Thus, with eye bleeding one needs to be able under normal circumstances would be viewed as a large patch of blood absent being able to ascertain where the leak is coming from and then where it spreads out to so that one can go in with a laser and seal just a small portion of the retina to stop the leak.

In order to obtain good retinal images, one needs to have sufficient illumination and for various retinal cameras with associated optical efficiencies and various fields of view, one requires illumination from 10 to several hundred watt seconds of white light. For this purpose, xenon strobe lamps are used, which have a temperature rating in terms of color that one has to correct for in order to obtain a white light image.

In normal practice the photographer decides at what point he or she wishes to take a picture and with a foot pedal or other button activates the camera. Once activated, the flash goes off and the picture is taken. Note that both manual and automatic activation of the strobes have been used in the past.

The most popular retinal camera is one made by Carl Zeiss, which was originally a film camera that dates back to the 1920s. The Zeiss FF-1 is a fairly old device, the major problem of which was obtaining enough flash output, namely enough power to reliably obtain a flash every 1.5 seconds. In the older cameras, a simple unregulated step-up transformer and unregulated capacitors were used to directly pump the flash lamp. Because of the variation of the load and the flash lamps utilized, the voltage applied to the flash varied significantly, which varied the flash lamp output from one strobe pulse to the next. Thus one could fire the strobe twice and one would not necessarily obtain the same exposure due to the unregulated transformer and the unregulated capacitors. Since the capacitors were unregulated, there could be as much as 30% variance with each shot.

Carl Zeiss in later years tried to solve these problems, finally utilizing semiconductor switching. These later models required an exceptionally large transformer that could generate more voltage and handle more current than the predecessor models. The result was that in the later Zeiss retinal cameras, Zeiss was able to reliably provide capacitor discharge at a regulated voltage.

The problem with these power supplies when used to power xenon flash lamps was that the power supply was relatively large and cumbersome, sometimes weighing in excess of 60 pounds and having an outside dimension of 4×5×3 feet.

Moreover, the bottleneck for all of the Zeiss power supplies was the step-up transformer.

Moreover, with transformers it is difficult to regulate the maximum voltage output. Typically for retinal camera applications the voltage should not exceed 500 volts. If the 500-volt output was exceeded due to variable loading, it was possible to blow up the capacitors used in the strobe bank, typically because even the best of the capacitors were and are rated for a maximum of 500 volts. Also, while rare, the xenon tube could also be damaged due to excessive voltage.

More importantly, one of the failings with the Zeiss power supplies was the fact that the power supplies would not be able to recharge the capacitor bank sufficiently fast to provide one flash per second. The problem in reducing the flash interval from 1.5 seconds to 1 second with a maximum strobe output was the advent of digital cameras. Utilizing film, one could obtain the one-second intervals for the strobes because one could use less than full power in the flash lamps. However, with the use of digital cameras having increased resolution came the need for higher flash outputs. It is noted that with higher resolution one has smaller pixels; and with smaller pixels, the individual pixels do not see as much light as the larger pixels. Thus there is a direct correlation between resolution and sensitivity. Although 11-megapixel cameras are now available, the standard retinal camera is a 6-megapixel device that requires the full 500 volts across the strobe to produce the required maximum flash output.

Thus, with transformer-based power supplies, since the resolution increases with the number of pixels in the camera, the higher the output of the strobe had to be, the longer would be the recharge time for the capacitors. As a result, for higher-power strobes it was virtually impossible to obtain one-flash-per-second strobing.

Not only was it deemed desirable to eliminate the transformer and to reduce the size and weight of the system, there was a problem with increasing the efficiency and, more importantly, lowering the electromagnetic interference/electromagnetic compatibility (EMI/EMC) that was the result of utilizing transformer-based power supplies.

Moreover, with transformers there were only a limited number of methods for controlling the charging of the strobe capacitor bank and the output of the bank.

SUMMARY OF INVENTION

In the subject system, the power supply for the retinal camera is a transformerless power supply operating directly off line voltage, which, because of the elimination of the transformer, results in increased efficiency and lowers EMI/EMC problems.

In order to obtain constant 500-volt charging of the strobe capacitor bank, a hybrid voltage multiplier is connected to normal 120-volt line voltage. In one embodiment the voltage multiplier uses a combination of an AC coupling circuit and a half-wave rectifier to develop the required voltage by adding this half-wave rectified DC voltage to the waveform coupled out of the AC coupling circuit. This voltage is then applied to a pass device coupled to a controller to provide a regulated voltage to the flash lamp capacitors. The combination of an AC coupling circuit and a half-wave rectifier in the hybrid voltage multiplier in one embodiment acts to provide a 340-volt peak-to-peak signal to which is added a 170 DC volt bias to provide for the 500-volt-plus output. This output is applied to a unidirectional pass element, in one embodiment including a hysteresis switch that utilizes a sensed voltage input at the capacitor bank and turns the pass element off when a predetermined voltage level has been exceeded and turns it on when the sensed voltage drops below this voltage by a predetermined voltage. Thus the unidirectional pass element is turned on when the voltage at the input to the capacitor bank falls below a predetermined level that determines the hysteresis of the system.

The voltage applied to the xenon flash lamp is obtained by switching the outputs of the capacitors of the capacitor bank so that whether the xenon flash lamp is operated at maximum output or less, the voltage applied to the flash lamp is constant for correct exposure and available once per second.

In operation, by half-wave rectifying the positive-going portions of the line voltage and adding them to the AC-coupled waveform one obtains a 500-volt output, which is passed through the unidirectional pass element, in one embodiment a high-power PNP bipolar transistor.

The pass elements can also be composed of NPN bipolar transistors, MOSFET P-channel transistors, MOSFET N-channel transistors, Insulated Gate Bipolar Transistors or IBGTs and thyristors.

Moreover, in one embodiment a controller is used for hysteresis control of the pass element.

The result is that by providing an AC charging current for the strobe bank, one is readily able to generate high voltage and to control the charging voltage for the strobe capacitors. Moreover, without using a transformer, one is able to use the subject voltage-multiplying techniques to obtain a reliable 500-volt-plus charging voltage. Note that the subject circuit cannot generate more than 500 volts regardless of the operation of the pass device. This results in effective overcharge protection. Additionally, because of the control available with bipolar transistors, SCRs and the like, one can with hysteresis control provide a highly controllable voltage source for the strobe capacitors.

The entire weight of the power supply can be limited to two pounds, with the supply itself, rather than being 60 pounds and 3 feet by 4 feet by 3 feet, being a reduced size 8-inch-by-8-inch-by-8-inch module.

Most importantly, the charging time for the capacitors can be made such that strobes can be flashed at once a second at maximum output, typically 720 watt seconds at 500 volts.

The result is highly regulated, high-power one-strobe-per-second strobe pulses, with a power supply that is 1/30 the weight of conventional power supplies and 1/6 the size. Moreover, because of the AC charging voltage, one can use a variety of unidirectional pass elements for improved voltage control.

In summary, a lightweight, small, high-voltage power supply for a xenon flash lamp or strobe permits rapid and reliable strobing for retinal imaging. In one embodiment the power supply can develop 500 volts at 720 watt seconds to permit firing the xenon strobe at full power one pulse per second. The power supply, rather than using heavy, bulky transformers, uses a hybrid high-voltage multiplier that involves an AC coupling circuit and a half-wave rectifier, the outputs of which are coupled in parallel to a capacitor bank to achieve a 500-volt charging source for the capacitor bank. This permits the capacitor bank to be charged with a continuous high voltage so that it can deliver a controlled, reliable high voltage to the xenon strobe.

BRIEF DESCRIPTION OF THE DRAWINGS

These and other features of the subject invention will be better understood in connection with a Detailed Description, in conjunction with the Drawings, of which.

DETAILED DESCRIPTION

Figure 1:
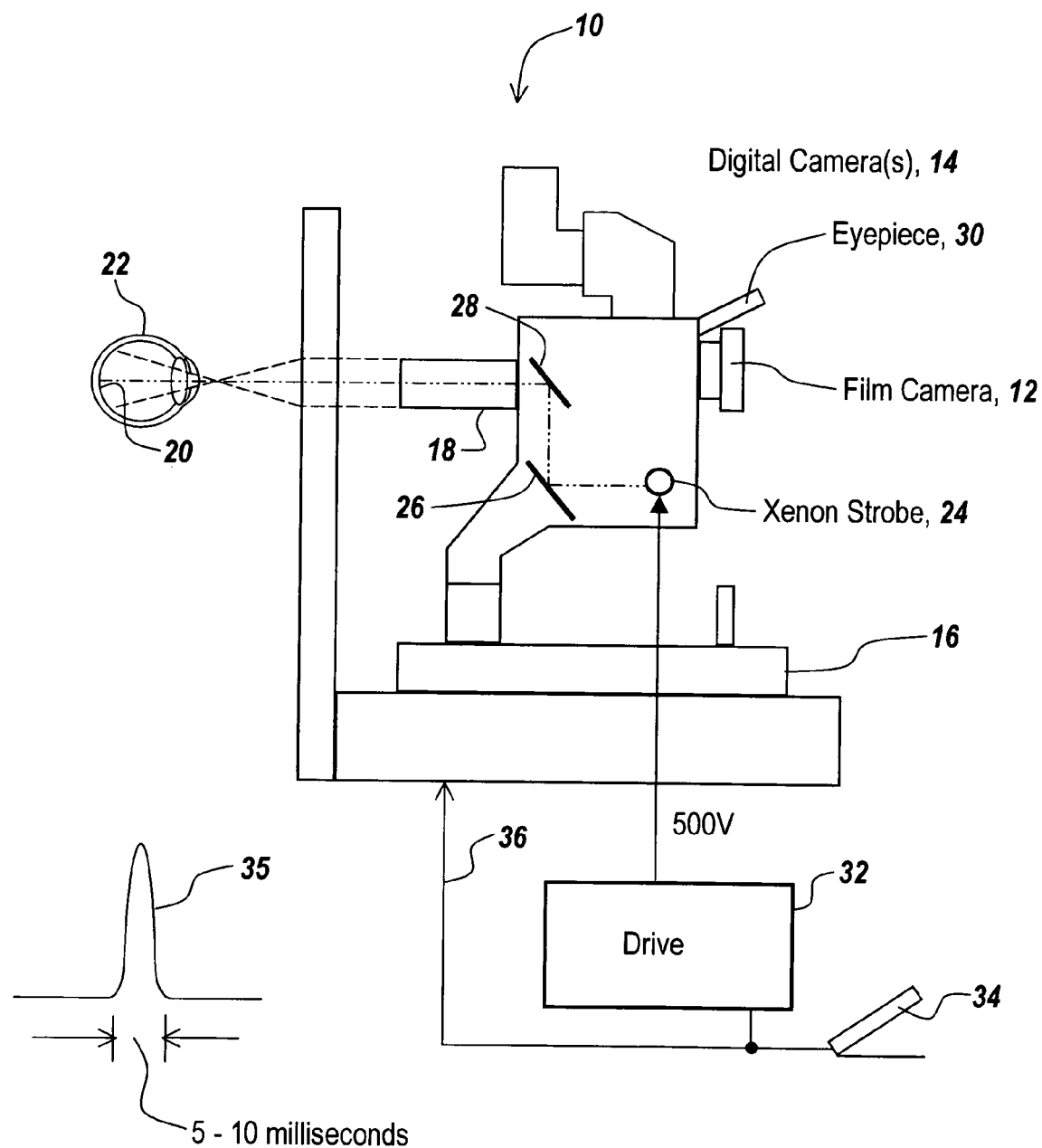
FIG. 1 is a diagrammatic illustration of the use of a retinal camera, with a 500-volt drive being applied to a xenon strobe to illuminate the retina of the eye.

Referring now to FIG. 1, a retinal imaging camera 10 includes a film camera 12 and a digital camera 14 mounted on a stand 16 such that an imaging system 18 images the retina 20 of eye 22 onto the focal planes of cameras 12 and 14. In order to illuminate retina 20, a xenon strobe lamp 24 has its output redirected by mirrors 26 and 28 out through imaging system 18 so that the output of xenon strobe 24 illuminates retina 20. Note that an eyepiece 30 is used for focusing both the digital and film camera as well as directing the optics to the appropriate portion of the eye.

Critical to the ability to illuminate the eye with strobe pulses every second with a precise maximum strobe output is a drive 32 that incorporates a power supply for delivering 500 volts to the xenon strobe. As illustrated, this is accomplished by delivery of a 500-volt pulse 35, with a pulse width of between 5 and 10 milliseconds. In one embodiment the strobe is flashed automatically at one-second intervals based on toggling of a foot switch 34, whereas in another embodiment the pulses from drive 32 are manually controlled by the foot switch.

It will be appreciated that foot switch 34 is also used to control camera 10 over line 36 to take the pictures such that any shuttering and exposure for either the film camera or the digital camera is controlled responsive to foot switch 34; or is actuated automatically if desired.

Key to the proper exposure of either the film in the film camera 12 or more importantly the CCD array of digital camera 14 is the ability to produce a reproducible, constant output from xenon strobe 24. As mentioned hereinbefore, digital cameras having a relatively high resolution require a maximum output for the xenon strobe. Note that the maximum output must be uniform in order for the exposures to be the same from picture to picture and must be available at one-second intervals. Thus, while in the past it was possible to expose film in camera 12 with xenon strobes operating at limited power to achieve the one-flash-per-second picture-taking rate, when utilizing increased-resolution digital cameras it is necessary to be able to reliably provide maximum power the xenon strobe once a second, e.g., 500 volts/720 watt seconds.

Figure 2:
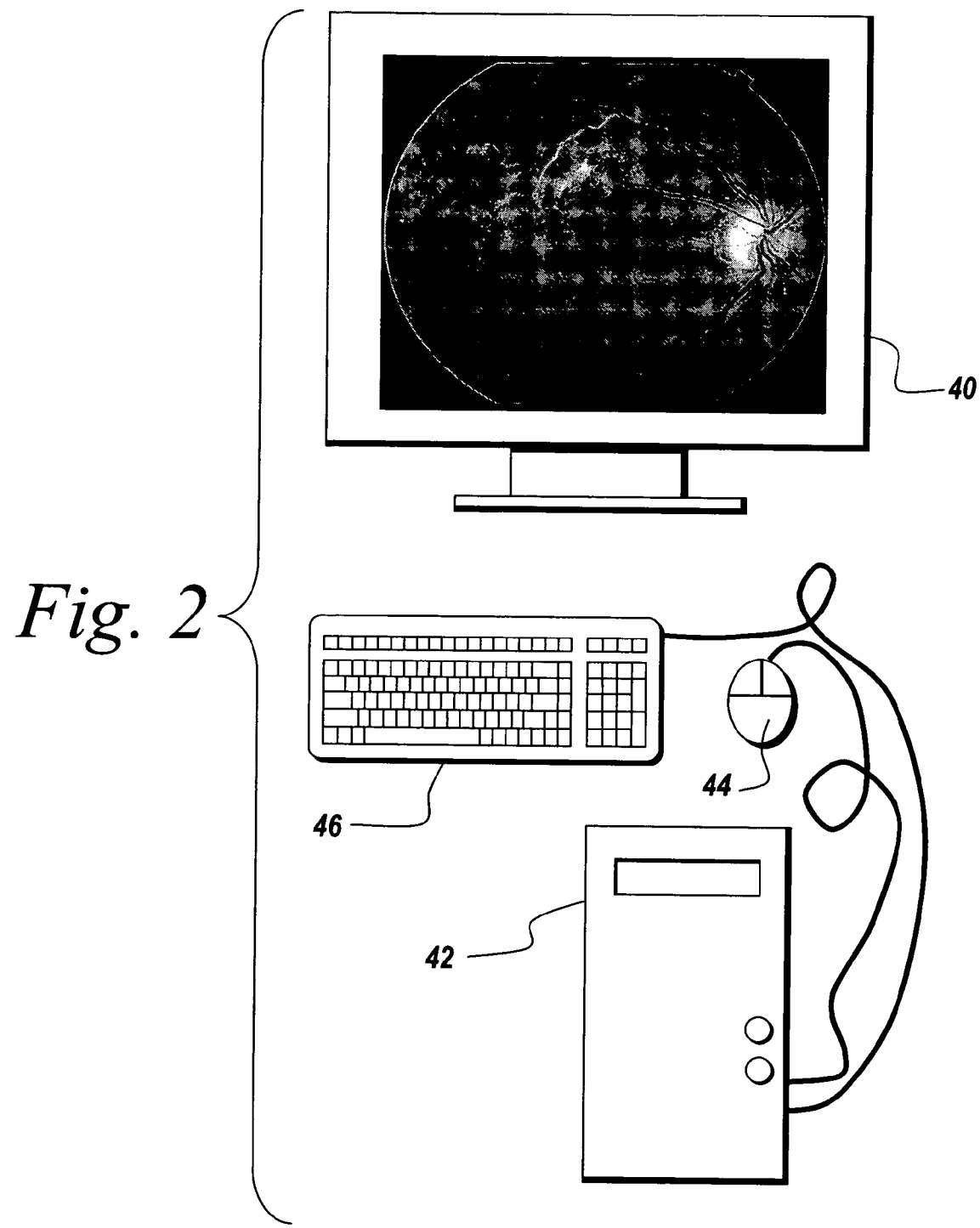
FIG. 2 is a diagrammatic illustration of a system for controlling the power to the xenon strobe of FIG. 1, illustrating the provision of a continuous high-voltage supply to a bank of capacitors under hysteresis control.

As illustrated in FIG. 2, a monitor 40 is used to display that which is imaged onto digital camera 10 in FIG. 1, with drive 32 having a computer 42 to set the output of the xenon strobe as illustrated by mouse 44. Likewise, the charge and distribution of power within the strobe capacitors in the strobe capacitor bank may be entered at keyboard 46.

Figure 3:
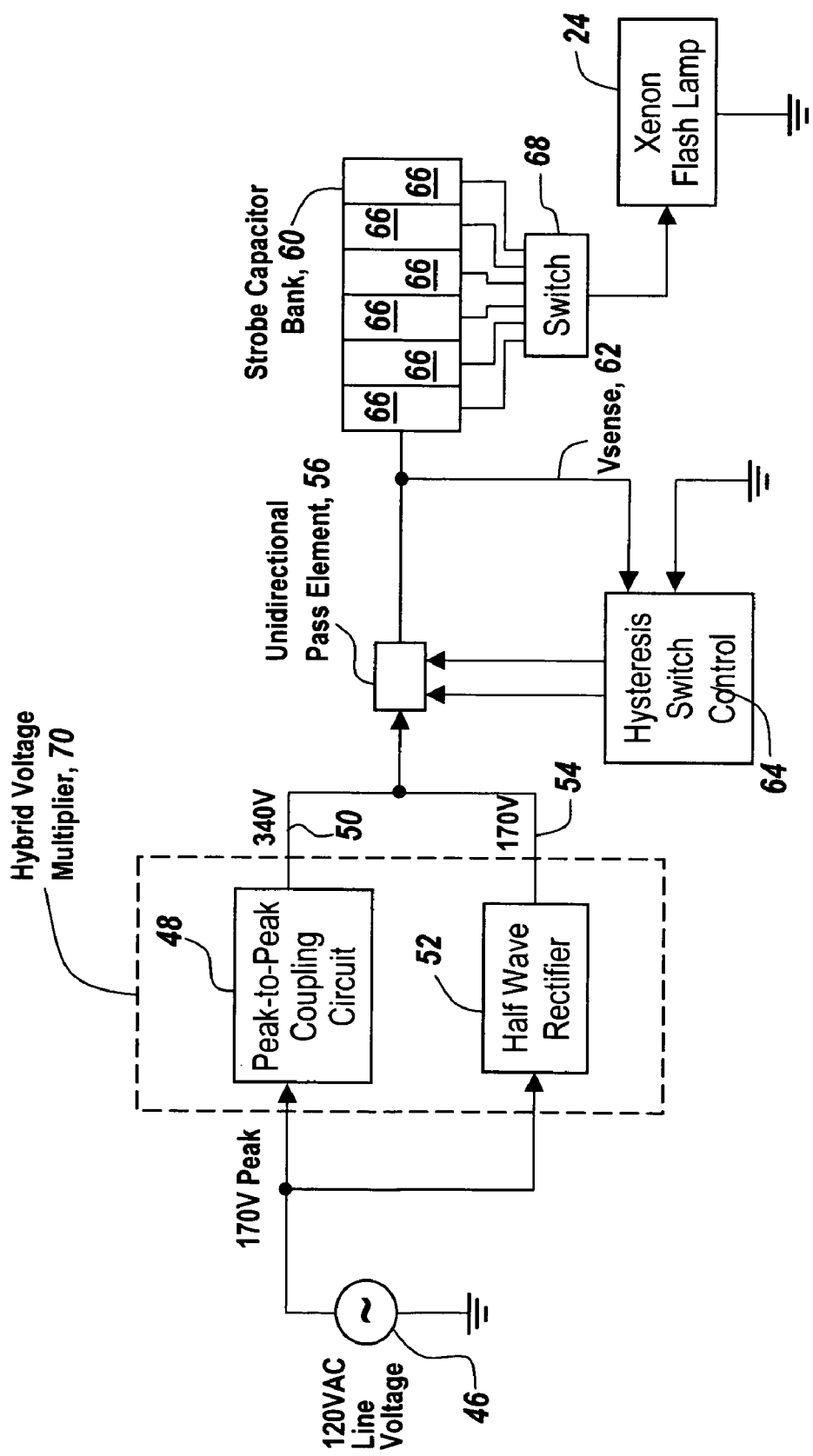
FIG. 3 is a block diagram of the subject power supply indicating both an AC coupling unit and a half-wave rectifier, the outputs of which are summed and provided through a pass element to a strobe capacitor bank for the powering the xenon flash lamp of FIG. 1.

As illustrated in FIG. 3, the power supply required for providing regulatable high voltages to the xenon flash lamp, rather than utilizing a step-up transformer, uses the 120-volt AC line voltage as illustrated at 46, which results in a 169.68-volt peak-to-peak AC voltage, rounded off to 170 volts peak-to-peak, that is AC coupled at 48 to provide an output voltage on line 50 of 340 volts peak to peak. The line voltage is also half-wave rectified at half-wave rectifier 52 to provide a DC output voltage of 170 volts as illustrated at 54.

These voltages are summed to provide a 510-volt charging voltage having an AC and DC component that is comprised of an 340 AC peak-to-peak voltage having its negative-going pulses shifted up by the 170 DC half-wave rectified voltage. The result is a 510-volt waveform coupled to a unidirectional pass element 56 that applies this voltage to a strobe capacitor bank 60 as illustrated. The capacitor bank voltage is sensed on line 62 that is applied to a hysteresis switch control 64 that turns the unidirectional pass element on and off depending on the sensed voltage. When the voltage exceeds a predetermined threshold, the pass element is turned off and is only turned on again when that voltage drops below a predetermined hysteresis point so that the charge voltage to the strobe capacitor bank is highly regulated.

Individual cells of strobe capacitor bank 60 are illustrated at 66 and are configured with different capacities such that when switched via switch 68 to xenon flash lamp strobe 24, the energy delivered to the flash lamp may be varied depending on which of the capacitors have their outputs switched to the flash lamp.

What will be appreciated is that by utilizing the 120-volt line voltage, one does not need to utilize heavy, cumbersome step-up transformers and the attendant difficulties to achieve the 500-volt-plus charging voltage for the strobe capacitor bank. Moreover, overcharging is completely eliminated because the charging voltage cannot go above 510 volts. This protects the capacitors in the 500-volt capacitor bank. In practice, voltage drops across the diodes in the hybrid multiplier circuit limit the actual maximum output voltage to under 500 volts.

The charging voltage can be further controlled and regulated by the unidirectional pass element to some voltage at or below the actual maximum charging voltage. The availability of a number of semiconductor switches provides considerable flexibility as to the overcharge control circuitry. Note, the unidirectional pass element, as will be discussed, can be a conventional high-power bipolar transistor, SCR or thyristor.

Not only is electromagnetic interference reduced by the elimination of the transformer, and not only are the size and weight of the transformer made a non-problem, variability of the charging voltage is eliminated due to the elimination of the step-up transformer.

As mentioned hereinbefore, the transformer voltage can fluctuate depending on the loading conditions and such problems are completely eliminated by the subject system.

Figure 4:
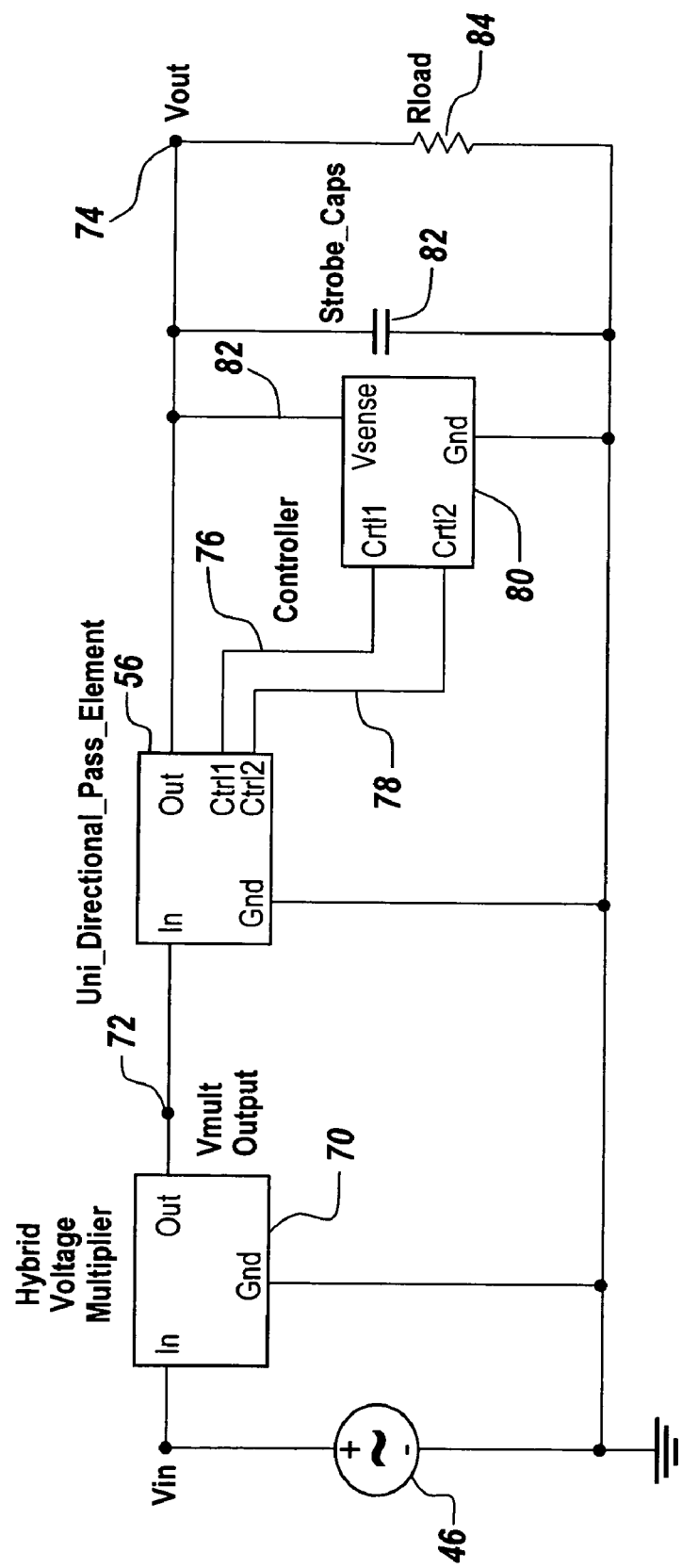
FIG. 4 is a block diagram of one embodiment of the subject power supply showing a voltage multiplier that incorporates the AC coupling circuit and half-wave rectifier of FIG. 3, a unidirectional pass element and a controller for the unidirectional pass element so as to control the connection of the output of the voltage multiplier to the strobe capacitors.

Referring now to FIG. 4, the peak-to-peak AC coupling circuit and half-wave rectifier of FIG. 3 are illustrated as being included in a hybrid voltage multiplier 70 having an input $V_{in}$ and an output $V_{mult}$ such that the output at point 72 is the aforementioned 500-plus voltage. This is applied to an input terminal of unidirectional pass element 56 that is controlled to either connect this $V_{out}$ voltage at 74 or interrupt it via signals on control lines 76 and 78 corresponding to Ctrl1 and Ctrl2. In one embodiment these control lines are selectively shorted through the use of a controller 80, which has an input a $V_{sense}$ line 82.

It will be appreciated that hybrid voltage multiplier 70, unidirectional pass element 56 and controller 82 are connected to system ground and that the strobe capacitor bank 60 is schematically illustrated at 82, whereas the xenon flash lamp is illustrated by load 84.

Figure 5A:
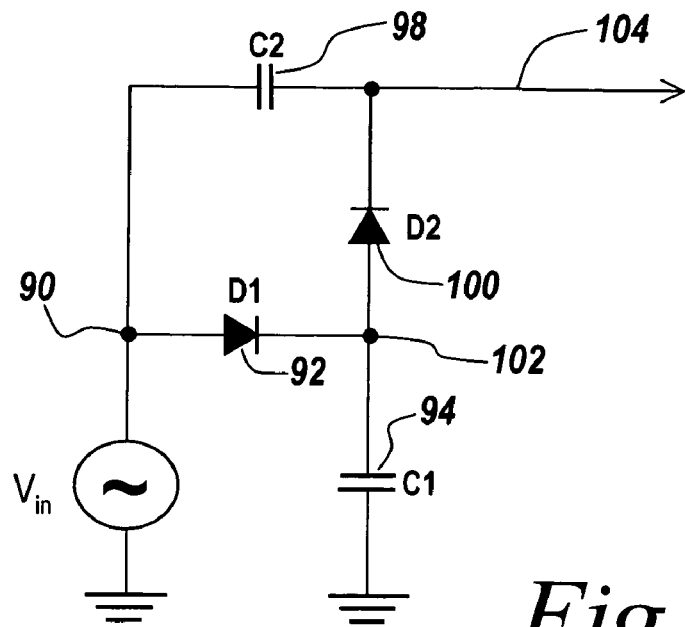
FIG. 5A is a schematic diagram of the voltage multiplier of FIG. 4, illustrating an AC coupler section and a half-wave rectifier section, the outputs of which are coupled together to form the output of the hybrid voltage multiplier.

Referring now to FIG. 5A, as to the hybrid voltage multiplier, a 120-volt line source is applied between input 90 and ground that results in a 170-volt positive peak and a 170-volt negative peak. This waveform is connected to the input between diode 92, D1 and capacitor 98, C2. Diode 94 and capacitor 94 in combination provide for half-wave rectifier or peak detector, causing capacitor 94 to charge up to a peak of +170 volts. For the negative peaks, diode 92 is reversed biased and it shuts off. Thus the voltage appearing at the junction 102 at the top of capacitor 94 and the anode of diode 100 is a positive 170 volts connected to the bottom of diode 100 at its anode. The cathode of diode 100 is connected to one side of capacitor 98. The other side of capacitor 98 is the line voltage. That circuit acts to prevent the negative-going waveform of the line voltage coupled through capacitor 98 from going below 170 volts. The result is the shifting of the 340-volt peak-to-peak signal up by 170 volts. The resulting output at 104 is a sine wave having a peak-to-peak amplitude of 340 volts, with the negative portion of the sine wave shifted up 170 volts. Thus the overall positive peak of this waveform at output 104 is at 510 volts.

The result is a 340-volt peak-to-peak waveform shifted up by half of the 120-volt line voltage coming in.

Figure 5B:
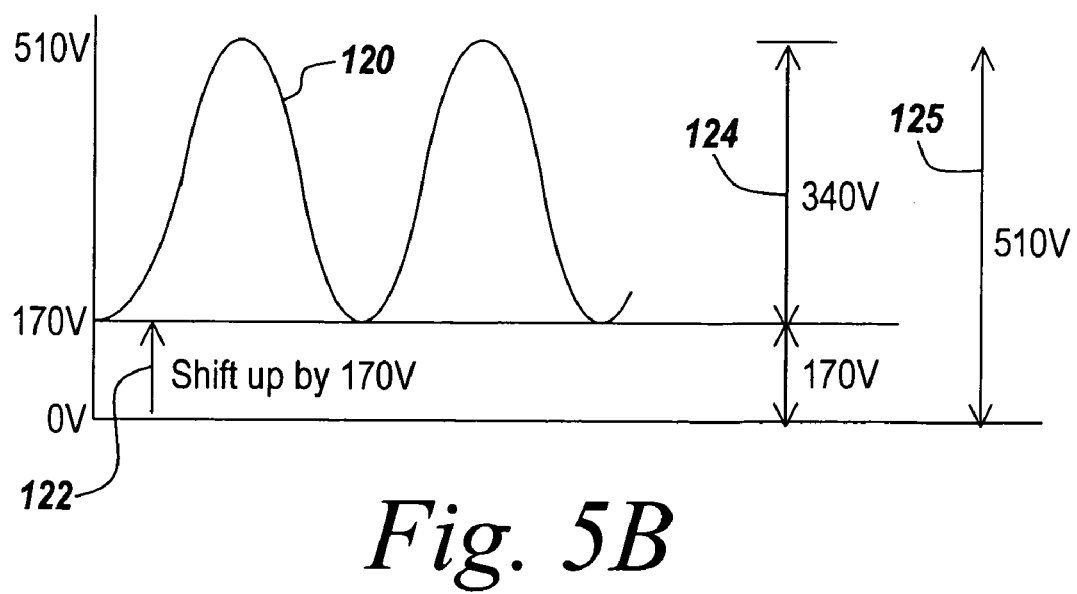
FIG. 5B is a waveform diagram illustrating the addition of the DC output of the half-wave rectifier to the AC-coupled portion of the line voltage to achieve a 510-volt output directly from the 120 AC line voltage; and, FIG. 6 is a block diagram of a hysteresis switch controller in which the capacitor voltage is sensed and a comparator is used to turn the unidirectional pass element of FIG. 4 on and off.

Referring to FIG. 5B, the input waveform 120 goes from plus 170 volts to a peak of 510 volts. The half-wave rectified offset of 170 volts is illustrated at 122, which is added to the input waveform having a peak-to-peak value of 340 volts as illustrated by arrow 124. When added as illustrated by arrow 126, the output voltage is the sum of the peak-to-peak line voltage and the half-wave rectified DC voltage, namely the aforementioned 510 volts.

Figure 6:
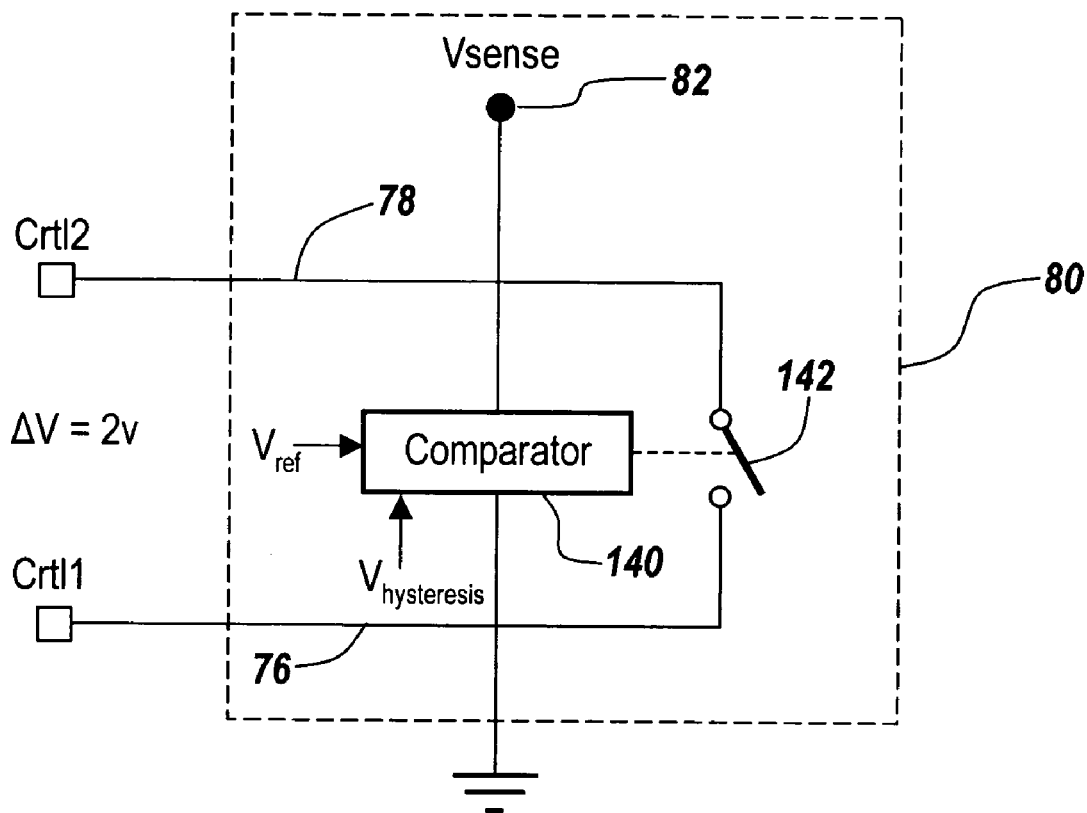

Referring to FIG. 6, controller 80 of FIG. 4 includes $V_{sense}$ terminal 82 and a comparator 140 that senses the voltage and produces requisite signals on control lines 76 and 78 which in one embodiment means shorting them. The controller is a form of a voltage regulator that can control a wide variety of semiconductor switch devices including bipolar transistors, SCR, MOSFETs and thyristors. In its simplest form controller 80 includes a comparator 140, which compares the voltage on $V_{sense}$ terminal 82 with $V_{ref}$, which in one case is, for instance, 480 volts to make sure that the 500-volt capacitor ratings are not exceeded. As long as $V_{sense}$ is below $V_{ref}$, switch 142 that shorts lines 76 and 78 together is left open as illustrated and the flash lamp capacitor charging continues.

When $V_{sense}$ is above $V_{ref}$, switch 142 is closed and the unidirectional pass device interrupts charging.

When, however, the sensed voltage falls below $V_{hysteresis}$, for instance, 278 volts, then switch 142 is opened and charging begins. In one embodiment, $V_{ref}$-$V_{hysteresis}$=2 volts.

In the case of the use of an SCR, control lines 1 and 2 are connected across the SCR's gate and cathode. When the sensed voltage rises to 480 volts in one embodiment, the SCR's gate is shorted to the cathode. This in and of itself will not shut off the SCR. However, when the input to the anode of the SCR drops below what the capacitor bank is charged to, which is connected to the cathode, the anode would be equal to or less than the voltage on the cathode and the SCR will turn off. The result is that the system has an effective 2-volt hysteresis, which is necessary to eliminate oscillations would the unidirectional pass device not be operated in a hysteresis mode.

Utilizing an SCR does, in fact, provide a small ripple on the voltage supplied to the strobe bank, which is more of a ripple than one would experience when using a transistor. Using a PNP transistor when one connects the base to the emitter, the transistor shuts off. If one did not introduce hysteresis as the capacitor is charged up and reaches the point at which the transistor was supposed to be shut off, it would only have to change by a millivolt and the transistor would turn back on. This would develop an oscillation. One introduces hysteresis or a dead zone to keep the circuit from oscillating at what is called the set point voltage.

Thus, as shown in FIG. 6, the difference between $V_{ref}$ and $V_{hysteresis}$ is a $\Delta v$ of 2 volts that is sufficient to prevent the aforementioned oscillation.

Another way to explain the hysteresis operation is to say that the voltage to the strobe capacitors is set to be regulated at a predetermined voltage, for instance 480 volts. The comparator closes switch 142 to turn off the supply to the capacitor bank by closing switch 142 when the sensed voltage is above 480 volts. Thus, switch 142 will close when the sensed voltage is at or greater than 480 volts, which disconnects the power supply from the strobe batteries and will re-open when the strobe voltage drops below 478 volts to activate the pass device for supplying voltage from the power supply to the bank of strobe capacitors. Thus for PNP unidirectional pass devices, closing switch 142 shuts the pass device off as it connects the base of the PNP transistor to its emitter.

In any event, a small amount of hysteresis is introduced into the pass device through controller 80 through a simple switching circuit, which shorts the Ctrl1 and Ctrl2.

In summary, what is shown is the ability to provide a regulated, constant high-voltage to rapidly charge a strobe capacitor bank. The system is flexibly constructed to be able to prevent overcharging of the batteries while at the same time providing a constant charging voltage directly from line current.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A lightweight, small, high-voltage power supply for a retinal imaging system using a rapidly strobed high-power flash lamp coupled to a capacitor bank, said flash lamp being rapidly strobed, comprising:

a transformerless high-voltage supply coupled to an AC line voltage and to said capacitor bank for supplying a continuously high voltage supply to said capacitor bank, whereby said flash lamp can be fired at full power at one pulse per second; and a unidirectional pass element between said transformerless high-voltage supply and said capacitor bank.

2. The power supply of claim 1, wherein said transformerless high voltage supply includes an AC coupling circuit and a half-wave rectifier coupled to said AC line voltage and having outputs coupled in series to said capacitor bank to achieve said high-voltage charging source for said capacitor bank.

3. The power supply of claim 2, wherein said AC coupling circuit includes a peak-to-peak coupling circuit.

4. The power supply of claim 1, and further including a voltage control circuit coupled to said unidirectional pass element, said control circuit including means for sensing the voltage at said capacitor bank and for controlling said pass element to interrupt the connection between said transformerless high-voltage supply and said capacitor bank responsive to said sensed voltage.

5. The power supply of claim 4, wherein said voltage control circuit includes a switching circuit having hysteresis for controlling said unidirectional pass element such that when said sensed voltage having exceeded a predetermined voltage to turn off said unidirectional pass element falls below a predetermined hysteresis level, said unidirectional pass element is turned on.

6. The power supply of claim 5, wherein said switching circuit includes a comparator coupled to a hysteresis-controlled switch, said comparator having said sensed voltage as one input thereto, a reference voltage as an input thereto and a predetermined hysteresis voltage as an input thereto, said hysteresis-controlled switch being closed when said sensed voltage is above said reference voltage, and being opened when said sensed voltage drops below said reference voltage by said predetermined hysteresis voltage.

7. The power supply of claim 6, wherein the difference between said reference voltage and said predetermined hysteresis voltage is 2 volts.

8. The power supply of claim 1, wherein said capacitor bank includes a number of capacitors and further including a power control switch for selectively switching said capacitors in series to said flash lamp.

9. The power supply of claim 1, wherein said transformerless high-voltage supply includes a hybrid voltage multiplier.

10. The power supply of claim 9, wherein said transformerless voltage multiplier includes an input coupled between said AC line voltage and ground, said voltage multiplier including an output and a first capacitor coupled between said input and said output, first and second series-connected diodes coupled between said input and said output, and a second capacitor coupled between the junction of said diodes and ground.

11. The power supply of claim 10, wherein said line voltage is 12 VRMS and 170 volts peak-to-peak, said hybrid voltage multiplier providing a voltage across said first capacitor of between 170 volts and 500 volts, said AC line voltage being shifted up by 170 volts by a half-wave rectification provided by said first diode and said second capacitor.

12. A method for reliably charging the flash lamp of a retinal camera to permit strobing at full power at one pulse per second, comprising:

providing a capacitor bank for driving the flash lamp;

providing a transformerless power supply coupled to an AC line voltage and to the capacitor bank for delivering a regulated high voltage to charge the capacitor bank at a continuous regulated predetermined high voltage, the capacitor bank being coupled to the flash lamp, whereby the inability to adequately control voltage from a high-voltage power supply using a transformer is avoided; and regulating the voltage supplied to the capacitor bank by interrupting the connection between the power supply and the capacitor bank when the voltage on the capacitor bank exceeds a predetermined level.

13. The method of claim 12, wherein the step of providing a transformerless power supply includes a half-wave rectifying the AC line voltage and AC coupling the AC line current in series with the half-wave rectified line current.

14. The method of claim 13, wherein the regulating step further includes providing a unidirectional pass element between the power supply and the capacitor bank.

15. The method of claim 14, wherein the regulating step further includes providing the unidirectional pass element with a semiconductor device and turning off the semiconductor device by the shorting together of two terminals thereof.

16. The method of claim 15, wherein the regulating step includes providing hysteresis in the turning on and off of the semiconductor device such that once a predetermined voltage on the capacitor bank has been exceeded to turn off the pass element, the pass element is turned on only after the sensed voltage at the capacitor bank drops below a predetermined hysteresis level.

17. A transformerless power supply for providing a regulated voltage to a capacitor bank directly from an AC line voltage to power the flash lamp in a retinal camera to permit full-power strobing of said flash lamp at once a second, comprising:

a hybrid voltage multiplier coupled to said AC line voltage, including a half-wave rectifier and an AC coupling circuit having outputs connected in series to produce said high voltage;

a unidirectional pass element including a semiconductor switch coupled between said hybrid voltage multiplier and said capacitor bank, said semiconductor switch turned off by shorting selected electrodes thereof; and, a high-voltage control circuit having one input coupled to said capacitor bank for turning said switch off when said sensed voltage is above a predetermined level.

18. The power supply of claim 17, wherein said control circuit includes an electrode shorting switch for shorting said electrodes and a hysteresis circuit for opening said electrode shorting switch once said electrode shorting switch has been closed only after said sensed voltage drops below said predetermined sensed voltage level by a predetermined hysteresis level.

\* \* \* \* \*